US011510664B2

(12) United States Patent
Mazzolino et al.

(10) Patent No.: US 11,510,664 B2
(45) Date of Patent: Nov. 29, 2022

(54) THORACIC STRUCTURE ACCESS APPARATUS, SYSTEMS AND METHODS

(71) Applicants: Gustavo Ignacio Mazzolino, Port Saint Lucie, FL (US); Federico Jose Benetti Rossi, Rosario (AR)

(72) Inventors: Gustavo Ignacio Mazzolino, Port Saint Lucie, FL (US); Federico Jose Benetti Rossi, Rosario (AR)

(73) Assignee: InVita Science Corp., Port St. Lucie, FL (US)

( * ) Notice: Subject to any disclaimer, the term of this patent is extended or adjusted under 35 U.S.C. 154(b) by 0 days.

(21) Appl. No.: 17/750,604

(22) Filed: May 23, 2022

(65) Prior Publication Data

US 2022/0273282 A1 Sep. 1, 2022

Related U.S. Application Data

(63) Continuation-in-part of application No. 17/553,992, filed on Dec. 17, 2021, now Pat. No. 11,369,357.

(60) Provisional application No. 63/199,780, filed on Jan. 25, 2021.

(51) Int. Cl.
*A61B 17/02* (2006.01)
*A61B 90/50* (2016.01)
*A61B 17/00* (2006.01)

(52) U.S. Cl.
CPC ...... *A61B 17/0206* (2013.01); *A61B 17/0293* (2013.01); *A61B 90/50* (2016.02); *A61B 2017/00407* (2013.01)

(58) Field of Classification Search
CPC ............... A61B 17/0206; A61B 2017/0237

USPC .................................................. 600/201–245
See application file for complete search history.

(56) References Cited

U.S. PATENT DOCUMENTS

| 4,852,552 | A | * | 8/1989 | Chaux | ............... | A61B 17/0206 |
| | | | | | | 600/234 |
| 11,369,357 | B1 | * | 6/2022 | Mazzolino | ......... | A61B 17/0206 |

* cited by examiner

*Primary Examiner* — Eduardo C Robert
*Assistant Examiner* — Tara Rose E Carter
(74) *Attorney, Agent, or Firm* — Francis Law Group

(57) ABSTRACT

A thoracic structure access system for retracting biological tissue and providing access to internal biological structures; particularly, intrathoracic structures, e.g., the heart and internal mammary arteries, to facilitate entry through the biological tissue with surgical instruments and interaction of the surgical instruments with the intrathoracic structures during a thoracic surgical procedure; particularly, minimally invasive CAGB and OPCAB procedures. The system facilitates coronary artery bypass graft (CAGB and OPCAB) procedures via a simple incision at a transxiphoid incision site and, hence, without fully transecting the sternum, i.e., performing a full sternotomy, or performing a thoracotomy. The system includes modular retractor and retention arm assemblies in communication with a ratchet assembly. When the system is disposed proximate a transxiphoid incision site and the modular retractor and retention arm assemblies are releasably engaged to opposing biological tissue portions at the transxiphoid incision site, the ratchet assembly can be actuated to apply opposing forces to the biological tissue portions to provide an access space at the transxiphoid incision site.

2 Claims, 8 Drawing Sheets

THORACIC STRUCTURE ACCESS APPARATUS, SYSTEMS AND METHODS

CROSS-REFERENCES TO RELATED APPLICATIONS

This application is a continuation-in-part of U.S. application Ser. No. 17/553,992, filed on Dec. 17, 2021, which claims the benefit of U.S. provisional patent application Ser. No. 63/199,780, filed Jan. 25, 2021.

FIELD OF THE INVENTION

The present invention relates to apparatus, systems and methods for accessing internal biological structures. More particularly, the present invention relates to thoracic structure access apparatus and systems, and minimally invasive methods employing same for accessing internal biological structures; particularly, intrathoracic structures at a transxiphoid incision site.

BACKGROUND OF THE INVENTION

It is well established that coronary artery disease (CAD); particularly, CAD associated with atherosclerosis of coronary arteries, is one of the most common major cardiovascular diseases affecting the global human population. CAD continues to be a predominant cause of death in both developed and non-developed countries. In 2015, approximately 110 million people were afflicted with CAD worldwide, and approximately 8.9 million died due to medical complications associated with CAD.

CAD characterized by atherosclerosis of one or more coronary arteries typically results in restricted and, hence, insufficient blood flow to the myocardium of the heart. In severe cases of CAD, acute restriction, or a complete obstruction of blood flow through one or more coronary arteries can, and often will result in myocardial infarction, i.e., heart failure.

Various procedures have thus been developed to treat CAD. One of the most common non-endovascular procedures for treating CAD comprises coronary artery bypass grafting (CABG), which involves excising an autologous blood vessel, e.g., an internal mammary artery, radial artery, and/or greater saphenous vein, from a pre-determined region of a subject's body for use as a vessel bypass graft to route blood flow distally to an obstructed region of a coronary artery.

As is well known in the art, conventional CABG procedures typically require opening the chest wall via a full sternotomy, and stopping a subject's heart and supporting the subject's cardiovascular system with a cardiopulmonary bypass (CPB) system.

As is also well known in the art, the above noted procedure steps associated with conventional CABG procedures are highly invasive, pose significant risk of operative complication and patient mortality, require lengthy hospitalization and are expensive with regards to short term and long-term treatment costs.

In an effort to address the above noted drawbacks associated with conventional CABG procedures, "minimally invasive" CABG procedures, i.e., CABG procedures that do not require opening the chest wall via a sternotomy and/or supporting the subject's cardiovascular system with a CPB system, have thus been developed. Such minimally invasive CABG procedures include off-pump coronary artery bypass (OPCAB) procedures, minimally invasive direct coronary artery bypass (MIDCAB) procedures, and the MINI off-pump coronary artery bypass (MINI OPCAB) procedure described in detail in U.S. Pat. No. 6,199,556, which was developed by Applicants.

Although conventional minimally invasive CABG procedures, including OPCAB, MIDCAB, and MINI OPCAB procedures, address most of the major drawbacks and disadvantages associated with such procedures, as discussed in detail below, there are still several major drawbacks and disadvantages associated with conventional minimally invasive CABG procedures.

A major drawback and, hence, disadvantage associated with an OPCAB procedure is that, although the procedure does not require stopping the heart and supporting the subject's cardiovascular system with a CPB system, a full thorax transection, i.e., full sternotomy, is still required.

A major drawback and, hence, disadvantage associated with MIDCAB procedures is that such procedures often require an incision to be made in the thorax between a subject's ribs or intercostal cartilage (i.e., a thoracotomy), which are often retracted to provide a surgeon with access to a subject's intrathoracic structures. The formation and retraction of thoracotomies is often associated with some of the same post-surgical maladies exhibited in subjects who have undergone a sternotomy, including severe post-surgical pain and respiratory complications.

Since MIDCAB procedures often employ robotic systems, further drawbacks and disadvantages associated with such procedures include substantial upfront cost of specialized robotic equipment and instruments, and substantial technical complexity with regards to robotically assisted techniques and associated thoracoscopic techniques, which often require considerable additional training for surgeons. Surgeons also often struggle with the lack of haptic feedback associated with robotically assisted techniques and associated thoracoscopic techniques, limiting working centers and surgical procedures.

MINI OPCAB procedures, such as disclosed in U.S. Pat. No. 6,199,556, substantially reduce and, in some instances, eliminate the above referenced major drawbacks associated with OPCAB and MIDCAB procedures. However, although MINI OPCAB procedures reduce and, in some instances, eliminate the above referenced major drawbacks associated with OPCAB and MIDCAB procedures, there are still several drawbacks associated with MINI OPCAB procedures.

As discussed in detail below, MINI OPCAB procedures employ a thoracic structure access apparatus (commonly referred to as a "retractor") to provide access to a thoracic cavity or opening at a transxiphoid incision site (also deemed and referred to herein as "a lower partial sternotomy site").

Since conventional thoracic structure access apparatus, such as disclosed in U.S. Pat. Nos. RE34,150 and 4,627,421, are specifically designed and configured for full thoracic transections, such access systems can, and often will, apply excessive forces to biological tissue proximate a transxiphoid incision site. The excessive forces can, and often will, traumatize tissue and, thereby, associated biological structures proximate the transxiphoid incision site.

Indeed, the continuous application of excess forces to biological tissue proximate a transxiphoid incision site by a thoracic structure access apparatus can, and often will, induce ischemia of the biological tissue proximate to and distant from the transxiphoid incision site due to elevated tissue pressure and/or compressed nerves and blood vessels. The thoracic structure access apparatus also traumatizes biological tissue by compressing nerves, and compressing blood vessels and, thereby, causing ischemia in biological tissues.

Such tissue and structure trauma increases the post-surgical recovery time of a patient and increases the probability of post-surgical complications, such as inflammation and/or infection of the tissue.

Further, the thoracic structure access apparatus and systems employed to perform a MINI OPCAB procedure are often cumbersome, complex, and excessively difficult for a surgeon to employ before and during a MINI OPCAB procedure.

It would thus be desirable to provide thoracic structure access apparatus and systems, and surgical procedures employing same; particularly, CABG and OPCAB procedures, which substantially reduce or eliminate the drawbacks and disadvantages associated with conventional thoracic structure access apparatus and systems, and surgical procedures employing same; particularly, CABG and OPCAB procedures.

It is therefore an object of the invention to provide improved thoracic structure access apparatus and systems, and surgical procedures employing same; particularly, CABG and OPCAB procedures, which substantially reduce or eliminate the drawbacks and disadvantages associated with conventional thoracic structure access apparatus and systems, and surgical procedures employing same; particularly, CABG and OPCAB procedures.

It is a further object of the present invention to provide thoracic structure access apparatus, systems and methods that can be readily employed to facilitate various thoracic surgical procedures in a simple and economical manner.

It is a further object of the present invention to provide thoracic structure access apparatus, systems and methods that can be readily employed to substantially reduce or eliminate trauma of biological tissue associated with tissue retraction during a surgical procedure; particularly, a CABG and/or OPCAB procedure.

It is a further object of the present invention to provide thoracic structure access apparatus and systems that facilitate CABG and OPCAB procedures via a simple incision at a transxiphoid incision site and, hence, without fully transecting the sternum, i.e., performing a full sternotomy, or performing a thoracotomy.

It is a further object of the present invention to provide thoracic structure access apparatus and systems that provide access to cardiovascular structures, including a beating heart, during a CABG and/or OPCAB procedure in a minimally invasive manner.

SUMMARY OF THE INVENTION

The present invention provides improved thoracic structure access apparatus and systems, and minimally invasive methods for accessing intrathoracic biological tissue structures of a subject via an incision (referred to herein as a "xiphoid incision" and "transxiphoid incision") at a transxiphoid incision site with same during surgical procedures; particularly, CABG and OPCAB procedures.

The thoracic structure access apparatus and systems are optimal for retracting biological tissue proximate the transxiphoid incision site and, thereby, accessing and viewing intrathoracic structures of a subject, including a subject's "beating" heart, during surgical procedures with minimal biological tissue trauma.

In a preferred embodiment of the invention, the thoracic structure access systems of the invention comprise a tissue retractor system, i.e., an offset retractor assembly, configured and adapted to provide access to intrathoracic structures of a subject through a xiphoid incision proximate a xiphoid process and without fully transecting a sternum, the tissue retractor system comprising a tissue retractor arm assembly, a tissue retention arm assembly, and a linear ratchet assembly.

In one embodiment of the invention, the tissue retractor arm assembly comprises a first elongated arm region, a first coupling member, and a first elongated mid-arm region disposed between and connecting the first elongated arm region and the first coupling member, the first coupling member being positioned substantially perpendicular to the first elongated arm region and first coupling member, the tissue retention arm assembly comprising a second elongated arm region, a second coupling member, and a second elongated mid-arm region disposed between and connecting the second elongated arm region and the second coupling member, the second coupling member being positioned substantially perpendicular to the second elongated arm region and second coupling member, the ratchet assembly comprising a crossbar, a first ratchet sub-assembly, and a second ratchet sub-assembly, the first ratchet sub-assembly comprising a first handle assembly and a first pinion assembly, the second ratchet sub-assembly comprising a second handle assembly and a second pinion assembly, the first ratchet sub-assembly slidably engaged to the crossbar and adapted to rotatably engage the first coupling member, whereby the first pinion assembly is in communication with the first coupling member, wherein, when the first pinion assembly is rotated, the first coupling member rotates and induces first angular articulation of the first elongated arm region, the second ratchet sub-assembly engaged to the crossbar and adapted to rotatably engage the second coupling member, whereby the second pinion assembly is in communication with the second coupling member, wherein, when the second pinion assembly is rotated, the second coupling member rotates and induces second angular articulation of the second elongated arm region, the first handle assembly is operatively connected to the first ratchet sub-assembly and adapted to induce first lateral motion of the first ratchet sub-assembly and, thereby, the tissue retractor arm assembly in first and second directions in a first plane substantially parallel to the longitudinal axis of the ratchet assembly, whereby the tissue retractor arm assembly transitions over a first plurality of retractor arm assembly tissue engaging positions when the first coupling member is connected to the first ratchet sub-assembly, the second handle assembly is operatively connected to the second ratchet sub-assembly and adapted to induce second lateral motion of the second ratchet sub-assembly and, thereby, the tissue retention arm assembly in third and fourth directions in a second plane substantially parallel to the longitudinal axis of the ratchet assembly, whereby the tissue retention arm assembly transitions over a first plurality of retention arm assembly tissue engaging positions when the second coupling member is connected to the second ratchet sub-assembly, the first elongated arm member of the tissue retractor arm assembly comprising at least a first tissue retractor member configured and adapted to releasably engage first biological tissue proximate the xiphoid incision when the tissue retractor arm assembly is in at least a first retractor arm assembly tissue engaging position, the second elongated arm member of the tissue retention arm assembly comprising at least a second tissue retractor member configured and adapted to releasably engage second biological tissue proximate the xiphoid incision when the tissue retention arm assembly is in at least a first retention arm assembly tissue engaging position, the tissue retractor arm assembly and the tissue retention arm assembly, when connected to the ratchet assembly and the engaged to the first and second biological tissue, being configured and adapted to dispose the first and second biological tissue a spaced distance apart, wherein an open access space proximate the subject's xiphoid process is provided, and jointly and uniformly lift opposing portions of a thoracic cage.

In one embodiment of the invention, the tissue retractor system similarly comprises a tissue retractor arm assembly, a tissue retention arm assembly, and a linear ratchet assembly. However, in the noted embodiment, the tissue retractor system further comprises a first rotatable ratchet assembly and a second rotatable ratchet assembly.

In the noted embodiment, the tissue retractor arm assembly comprises a first elongated arm region and a first base region connected thereto, the first base region comprising a first rotatable ratchet gear disposed on the distal end of the first base region, the tissue retention arm assembly comprising a second elongated arm region and a second base region connected thereto, the second base region comprising a second rotatable ratchet gear disposed on the distal end of the second base region, the ratchet assembly comprising a crossbar, a first ratchet sub-assembly and a second ratchet sub-assembly, the first ratchet sub-assembly being slidably connected to the crossbar, the first ratchet sub-assembly comprising a first coupling member and a first handle assembly, the distal end of the first coupling member comprising a first geared end configured and adapted to slidably engage the first rotatable ratchet gear of the first base region, wherein the first coupling member is allowed to rotate and induce first angular articulation of the first elongated arm region, the second ratchet sub-assembly comprising a second coupling member, the second ratchet sub-assembly being statically connected to the crossbar, the distal end of the second coupling member comprising a second geared end configured and adapted to slidably engage the second rotatable ratchet gear of the second base region, wherein the second coupling member is allowed to rotate and induce second angular articulation of the second elongated arm region, the first handle assembly is operatively connected to the first ratchet sub-assembly and adapted to induce first lateral motion of the first ratchet sub-assembly and, thereby, the tissue retractor arm assembly in first and second directions in a first plane substantially parallel to the longitudinal axis of the ratchet assembly, whereby the tissue retractor arm assembly transitions over a plurality of retractor arm assembly tissue engaging positions when the first coupling member is the engaged to the first base region, the first elongated arm member of the tissue retractor arm assembly comprising at least a first tissue retractor member configured and adapted to releasably engage first biological tissue proximate a xiphoid incision when the tissue retractor arm assembly is in at least a first retractor arm assembly tissue engaging position, the tissue retractor arm assembly and the tissue retention arm assembly, when connected to the ratchet assembly and the engaged to the first and second biological tissue, being configured and adapted to dispose the first and second biological tissue a spaced distance apart, wherein an open access space proximate the subject's xiphoid process is provided, and jointly and uniformly lift opposing portions of a thoracic cage.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1A:
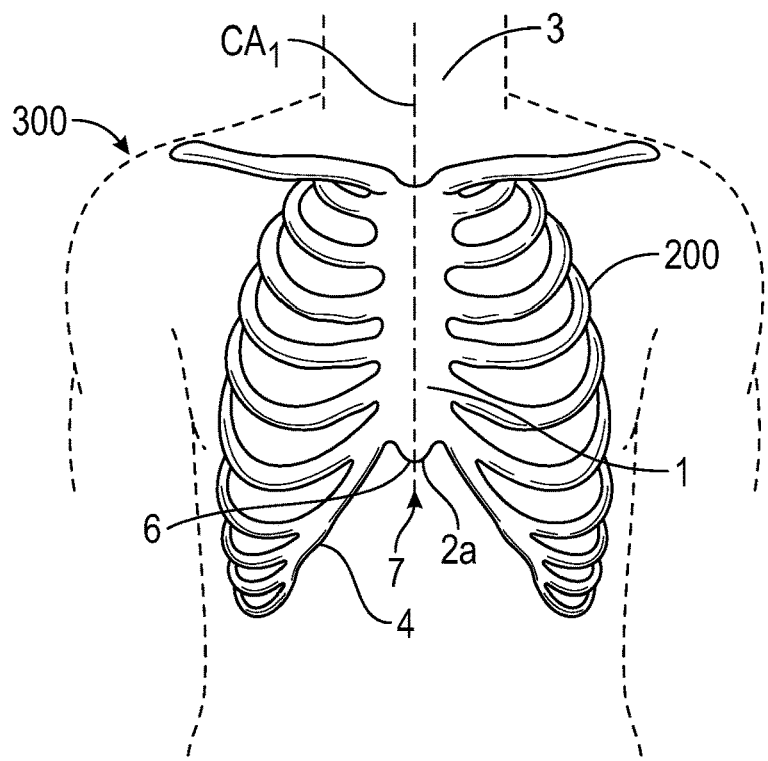
FIG. 1A is an illustration of a subject's thorax showing a transxiphoid incision site and a xiphoid incision therein.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that, although the present invention is described and illustrated in connection with coronary artery bypass grafting (CABG and OPCAB) procedures; particularly, MINI off-pump coronary artery bypass (MINI OPCAB) procedures, the invention is not limited to such procedures. According to the invention, the apparatus, systems and methods of the invention can also be employed to provide access to internal structures; particularly, intrathoracic structures at a transxiphoid incision site during other surgical procedures, e.g., ventricle restoration, heart valve replacement procedures, etc.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "tissue" and "biological tissue" are used interchangeably herein, and mean and include mammalian biological tissue, such as, by way of example, pleural tissue and cardiac tissue.

The term "minimally invasive", as used herein in connection with coronary artery bypass grafting; particularly, a CABG and OPCAB procedure, means and includes a CABG and/or OPCAB procedure that does not comprise the step of fully transecting the sternum or thorax of a subject, i.e., performing a full sternotomy. The term "minimally invasive" also means and includes CABG and OPCAB procedures that do not comprise the steps of stopping a subject's beating heart and supporting the subject's cardiovascular system with a cardiopulmonary bypass (CPB) device.

The terms "xiphoid incision" and "transxiphoid incision" are used interchangeably herein, and mean and include a surgical incision proximate to, but not necessarily directly above, the xiphoid appendage (also referred to herein as a "xiphoid process") of a subject's sternum. The terms "xiphoid incision" and "transxiphoid incision" thus mean and include a "lower partial sternotomy incision".

The term "transxiphoid incision site", as used herein, thus, means and includes a surgical field proximate a subject's thorax, which provides access to intrathoracic biological tissue structures of a subject via, for example, a "xiphoid incision".

The term "retraction", as used herein, means and includes the drawing apart of or parting of incised or transected biological tissue to provide access to internal biological structures concealed by the biological tissue. The term "retraction", thus, in some instances, means and includes the drawing apart of or parting of thoracic tissue proximate a "transxiphoid incision site" to provide access to intrathoracic structures, e.g., a subject's heart.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, means that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to thoracic structure access apparatus, systems and methods for accessing internal biological structures; particularly, intrathoracic structures at a transxiphoid incision site.

More particularly, the present invention is directed to improved thoracic structure access apparatus and systems (also referred to as offset retractor assemblies) and methods for performing CABG and/or OPCAB procedures; particularly, MINI off-pump coronary artery bypass (MINI OPCAB) procedures.

In a preferred embodiment of the invention, the MINI OPCAB procedure developed by Applicants and disclosed in U.S. Pat. No. 6,199,556, which is expressly incorporated by reference herein, facilitates CABG and OPCAB procedures via a simple xiphoid incision, as defined herein (denoted "6" in FIG. 1A) at a transxiphoid incision site (denoted "7" in FIG. 1A) and, hence, without fully transecting the sternum, i.e., performing a full sternotomy or performing a thoracotomy. Access to and optimal visibility of a subject's "beating" heart at the transxiphoid incision site 7 during a MINI OPCAB procedure is achieved via a thoracic structure access apparatus and/or system.

Although conventional thoracic structure access apparatus and systems can be employed to perform minimally invasive CABG and OPCAB procedures, including MINI OPCAB procedures, as indicated above, such apparatus and systems are fraught with major drawbacks and disadvantages; particularly, a high risk of traumatized biological tissue and/or structures proximate to the transxiphoid incision site 7.

In view of the numerous drawbacks and disadvantages associated with conventional thoracic structure access apparatus and systems (and, hence, CABG and OPCAB procedures performed therewith), Applicants developed the xiphoid access apparatus and systems disclosed in U.S. Pat. No. 6,199,556.

Although the noted xiphoid access apparatus and systems, when employed properly, substantially reduce and, in many instances, eliminate the major drawbacks and disadvantages associated with conventional thoracic structure access apparatus and systems (and, thereby, CABG and OPCAB procedures performed therewith); particularly, the high risk of traumatized biological tissue and/or structures proximate to the transxiphoid incision site 7, as discussed below, there remains several drawbacks associated with the noted xiphoid access apparatus and systems.

A significant drawback associated with the xiphoid access apparatus and systems is that the noted apparatus and systems are generally cumbersome and complex, and, thus, excessively difficult for a surgeon to employ properly before and during a CABG and OPCAB procedure; particularly a MINI OPCAB procedure, which can, and often will, increase the risk of post-surgical complications, such as inflammation and/or infection of tissue, and, hence, post-surgical recovery time.

Indeed, it has been found that when the noted xiphoid access apparatus and systems are not employed properly, e.g., incorrectly mated to a subject's body, the tissue retraction arms of the xiphoid access apparatus can, and often will, traumatize biological tissue and structures, such as the costal cartilage, proximate a transxiphoid incision site 7 during tissue retraction.

The risk of incorrect mating of the noted xiphoid access apparatus and systems to a subject's body is exacerbated by virtue of the xiphoid access apparatus and systems requiring multiple ex situ or external mounting or securing points on one or more anatomical regions of a subject's body, such as the anatomical regions proximate the abdomen and the iliac crests of the subject. The xiphoid access apparatus and systems must thus be properly configured to accommodate the various sizes and configurations of a subject's body each time the xiphoid access apparatus and/or system are employed.

As will be readily apparent to one skilled in the art, the present invention provides improved thoracic structure access apparatus and systems (and, hence, CABG and OPCAB procedures employing same), which substantially reduce and, in several instances, eliminate the seminal drawbacks and disadvantages discussed above that are associated with conventional thoracic structure access apparatus and systems, as well as xiphoid access apparatus and systems disclosed in U.S. Pat. No. 6,199,556.

The thoracic structure access apparatus and systems (and, hence, minimally invasive CABG and OPCAB procedures employing same) of the invention are optimal for retracting biological tissue proximate a transxiphoid incision site and, thereby, accessing and viewing intrathoracic structures of a subject, including a subject's "beating" heart, during a CABG procedure with minimal biological tissue trauma.

In a preferred embodiment, the thoracic structure access apparatus and systems of the invention are adjustable and modular, i.e., comprise interchangeable components, and, thus, can be readily adapted to accommodate various sizes and dimensions of thoracic incision sites, more preferably, transxiphoid incision sites.

The adjustability and modularity of the thoracic structure access apparatus and systems of the invention provide a surgeon with significantly greater control with regards to the position of biological tissue pressure points proximate a transxiphoid incision site and the degree of force/pressure applied to the biological tissue pressure points.

According to the invention, the thoracic structure access systems of the invention can also be configured to accept a myriad of conventional complementary surgical attachments including, without limitation, beating heart stabilizers, mist blowers, suction tubes, suction stabilizer tubes, suture retainment members or hooks, surgical lights, and optical equipment, e.g., endoscopes.

As indicated above, although the present invention is particularly applicable to minimally invasive CABG and OPCAB procedures, and, hence, is described and illustrated in connection therewith; particularly, MINI OPCAB procedures, the invention is not limited to such procedures. According to the invention, the thoracic structure access apparatus and systems of the invention can also be employed to facilitate other surgical procedures, such as, by way of example, heart valve replacement procedures.

Figure 2A:
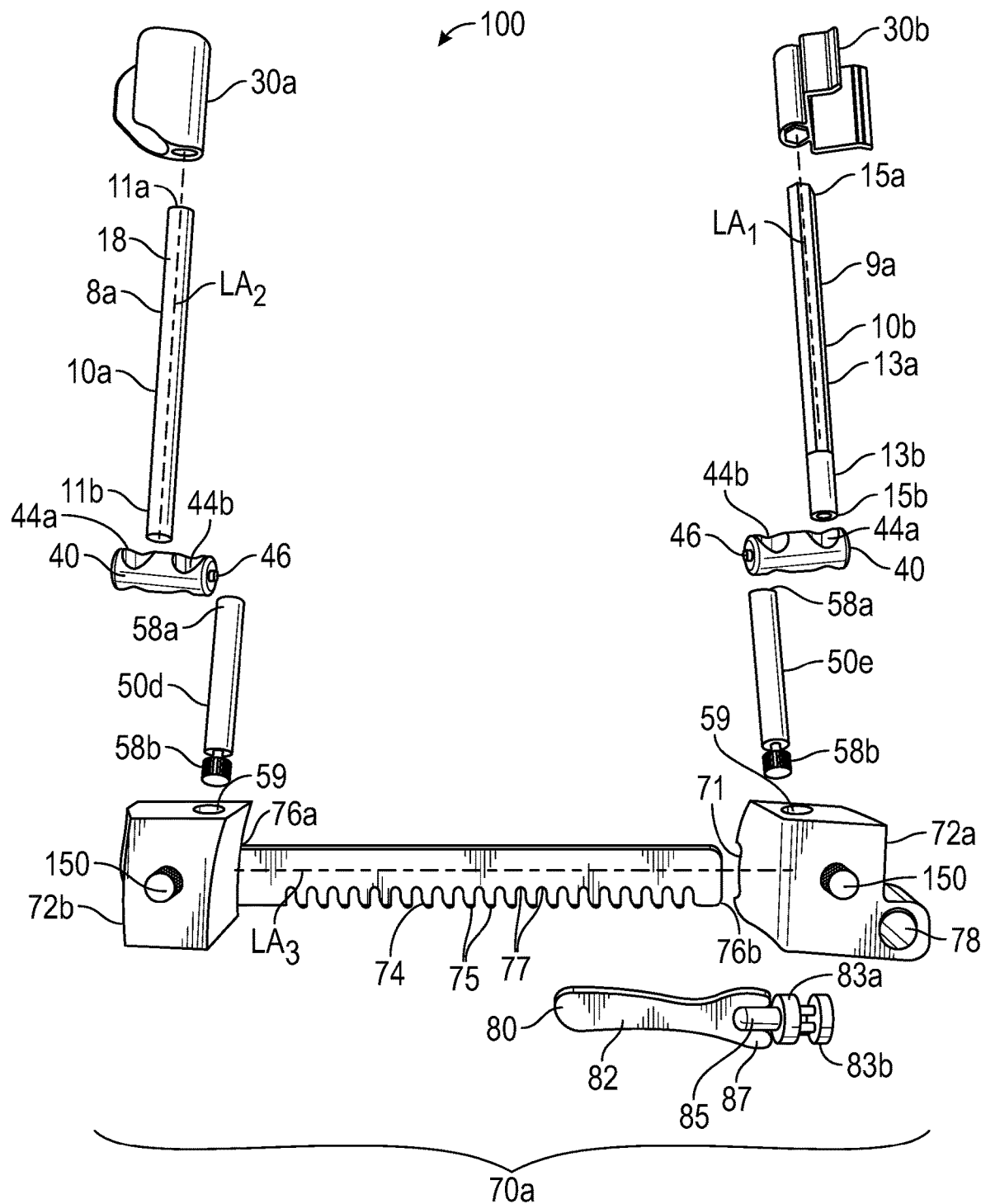
FIG. 2A is an exploded view of one embodiment of a thoracic structure access system, in accordance with the invention.

Referring now to FIG. 2A, there is shown one embodiment thoracic structure access system of the invention (denoted "100"). As illustrated in FIG. 2A, the thoracic structure access system 100 comprises a modular structure comprising a pair of arm assemblies, i.e., a retractor arm assembly 9a and a retention arm assembly 8a (also referred to herein as a "tissue retractor arm assembly" and "tissue retention arm assembly"), which are operatively connected to at least one arm assembly transverse motion inducing means, such as ratchet assembly 70a.

As indicated above and discussed in detail herein, the thoracic structure access system 100 is designed and configured to provide access to cardiovascular structures, including a beating heart, during thoracic surgical procedures; particularly, CABG and OPCAB procedures, via a simple xiphoid incision at a transxiphoid incision site, such as xiphoid incision 6 shown in FIG. 1A, i.e., minimally invasively.

Figure 1B:
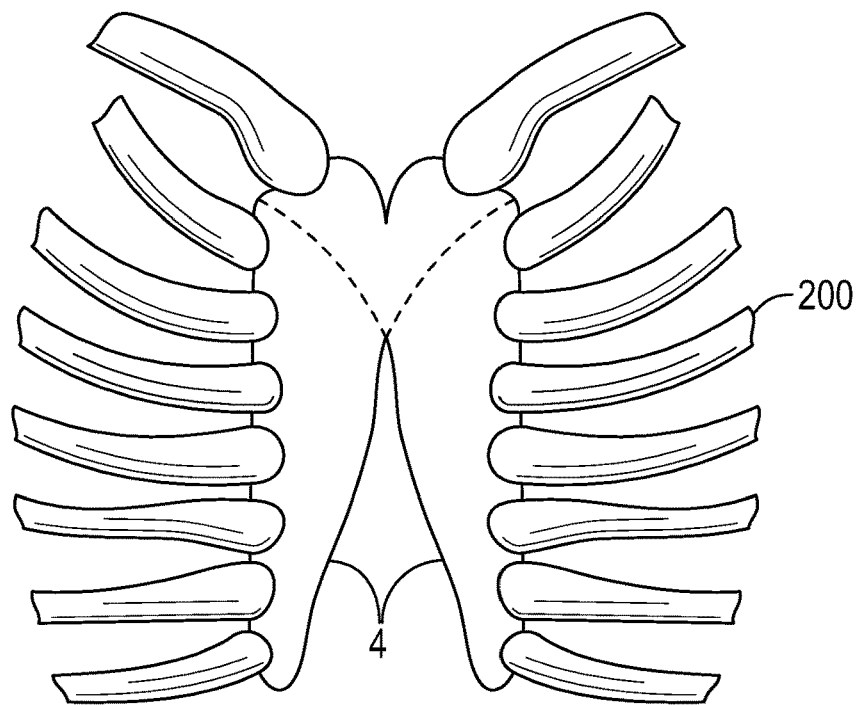
FIG. 1B is a further illustration of a subject's thorax showing a transxiphoid incision site with the lower and middle portion of the sternum spread and lifted.

In a preferred embodiment, the thoracic structure access system 100 (also referred to herein as "tissue retractor system") is specifically designed and configured to (i) spread biological tissue proximate an incision; particularly, a xiphoid incision, (ii) lift a thoracic cage, and (iii) lift at least the lower portion 4 of the sternum 200, as shown in FIGS. 1A and 1B, with minimal biological tissue trauma.

Referring now to FIG. 2A, in a preferred embodiment, the retention arm assembly 8a comprises elongated arm member 10a, interconnector member 40, and a coupling member 50d.

Figure 3:
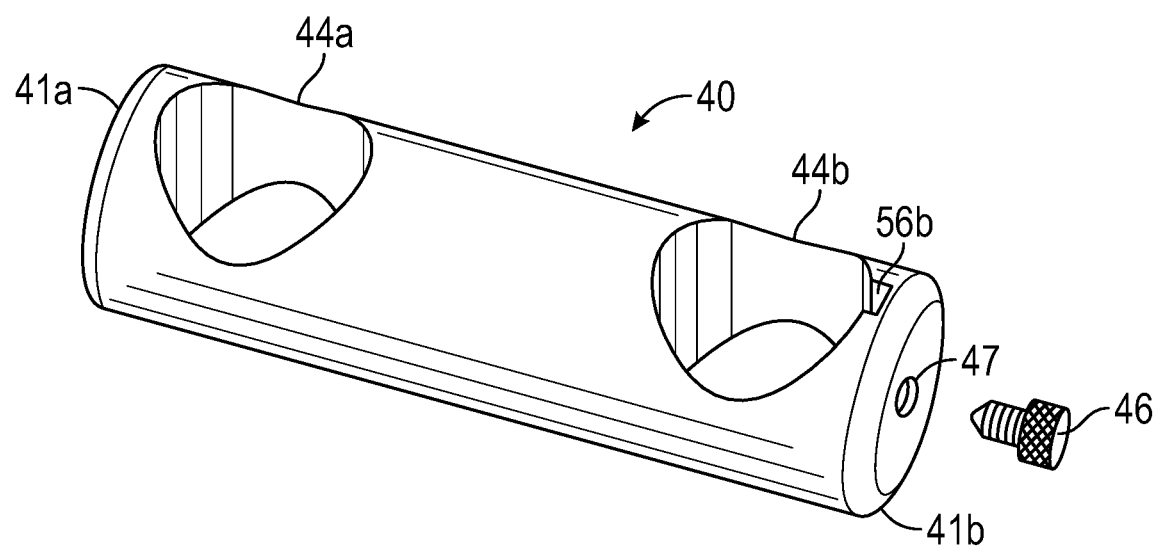
FIG. 3 is a perspective view of the interconnector member of the tissue retractor arm assembly shown in FIG. 2A, in accordance with the invention.

As illustrated in FIG. 3, in a preferred embodiment, the interconnector member 40 comprises two (2) receiving channels 44a, 44b. As discussed in detail below, in a preferred embodiment, receiving channel 44a is sized and configured to receive the distal ends 11b, 15b of elongated arm members 10a, 10b and receiving channel 44b is sized and configured to receive the proximal end 58a of coupling members 50d, 50e.

As set forth in priority U.S. application Ser. No. 17/553,992, in a preferred embodiment of the invention, the interconnector member 40 further comprises an arm/coupling member retention system that is configured and adapted to fix the coupling members 50d, 50e at a desired position (or positions) and abate rotation thereof.

As also set forth in priority U.S. application Ser. No. 17/553,992 and illustrated in FIG. 3, the interconnector member retention means comprises a set screw 46, more preferably, a pair of set screws 46.

As further illustrated in FIG. 3, to accommodate the set screws 46, the interconnector member 40 further comprises a pair of threaded holes 47 on the proximal and distal ends 41a, 41b thereof that are sized and configured to receive and cooperate with the set screw(s) 46.

As illustrated in FIG. 2A, in a preferred embodiment, the elongated arm member 10a is connected to the interconnector member 40, which, as set forth in priority U.S. application Ser. No. 17/553,992, facilitates rotation of the elongated arm member 10a in a substantially perpendicular plane relative to its longitudinal axis "$LA_2$" when the elongated arm member 10a is operatively connected to the interconnector member 40, and the coupling member 50d is engaged to the second ratchet sub-assembly 72b of ratchet assembly 70a and also connected to the interconnector member 40.

Figure 5:
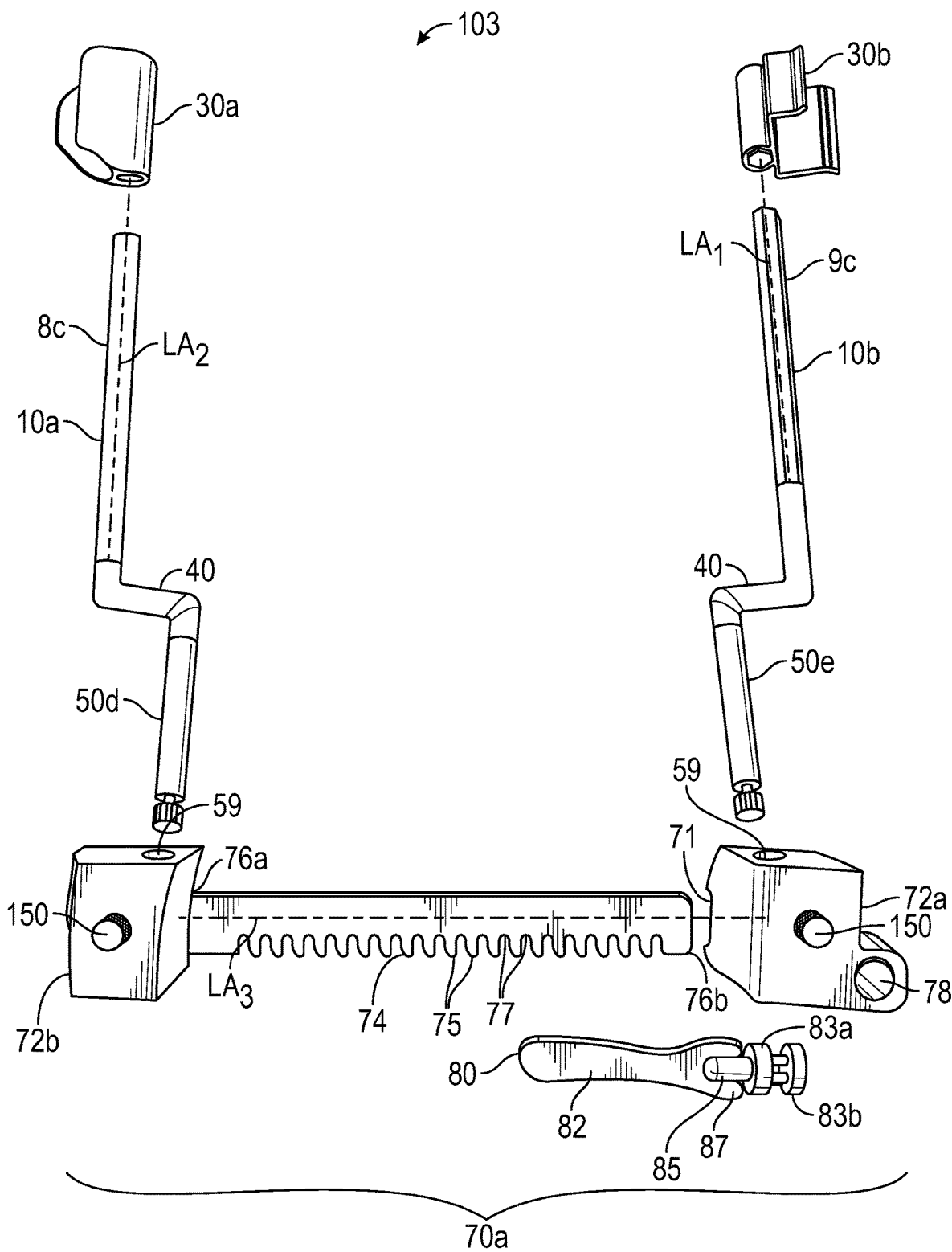
FIG. 5 is an exploded view of another embodiment of a thoracic structure access system, in accordance with the invention.

In some embodiments of the invention, the elongated arm member 10a, interconnector member 40, and coupling member 50d comprise integral members or sections of the retention arm assembly (denoted "8c" in FIG. 5), i.e., a single member, as shown in thoracic access system 103 illustrated in FIG. 5.

As further illustrated in FIG. 2A, the elongated arm member 10a further comprises at least one tissue retractor member of the invention (denoted "30a"), which is releasably engaged to the elongated arm member 10a.

As set forth in priority U.S. application Ser. No. 17/553,992, the tissue retractor member 30a is sized, configured, and adapted to releasably engage biological tissue proximate a xiphoid incision 6 at a transxiphoid incision site 7 when, as discussed in detail below, the thoracic structure access system 100 is actuated, whereby, the biological tissue is spread, i.e., disposed a spaced distance apart, and a thoracic opening is provided at the transxiphoid incision site 7.

Figure 4A:
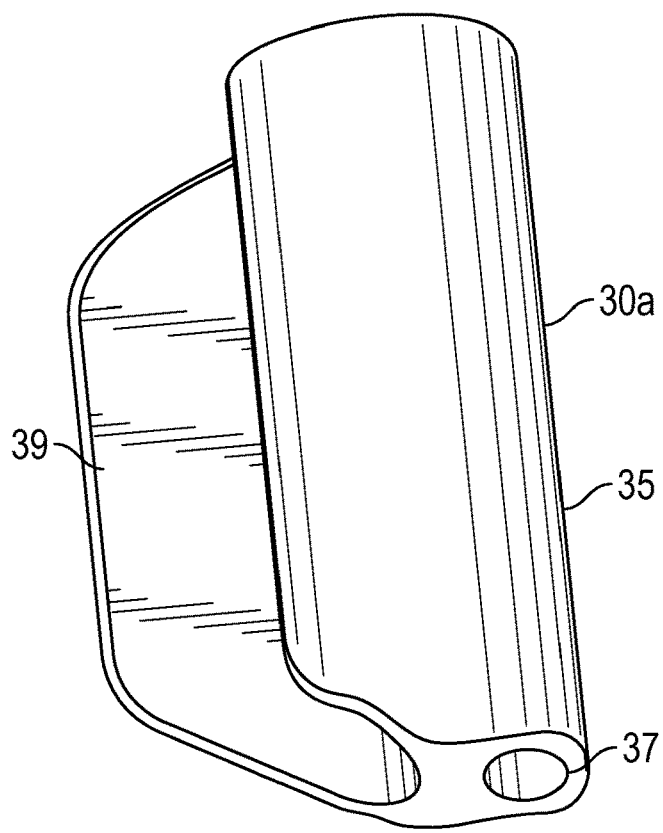
FIG. 4A is a perspective view of one embodiment of a tissue retractor member that is configured to engage biological tissue, in accordance with the invention.

As also set forth in priority U.S. application Ser. No. 17/553,992 and illustrated in FIG. 4A, the tissue retractor member 30a comprises an elongated arm member engagement end 35 comprising an arm member receiving channel or opening 37 that is sized and configured to receive the elongated arm member 10a therethrough, and a tissue engaging recess 39 that is sized and configured to receive and retain biological tissue therein.

According to the invention, the elongated arm member 10a can comprise textured features on at least a portion of the exterior surface 18 to abate movement, e.g., rotation, of the tissue retractor member 30a when positioned on the elongated arm member 10a.

As indicated above and illustrated in FIG. 2A, the retention arm assembly 8a comprises at least one tissue retractor member 30a. However, according to the invention, the retention arm assembly 8a can comprise a plurality of tissue retractor members 30a.

According to the invention, the tissue retractor member(s) 30a can be positioned at any suitable point along the length of the elongated arm member 10a.

As further illustrated in FIG. 2A, the retention arm assembly 8a is releasably engaged to the ratchet assembly 70a via a coupling member 50d.

In a preferred embodiment, the coupling member 50d comprises a proximal end 58a that is sized and configured to slidably translate into a receiving channel, i.e., receiving channel 44a or 44b, preferably, receiving channel 44b, of the interconnector member 40 to facilitate rotation of the interconnector member 40 and, thereby, the aforementioned rotation of the elongated arm member 10a when the elongated arm member 10a is operatively connected to the interconnector member 40.

As set forth in priority U.S. application Ser. No. 17/553,992 and illustrated in FIG. 2A, the coupling member 50d further comprises a gear-tipped distal end 58b that is sized and configured to be received in and releasably engage coupling member channels 59 of first and second ratchet sub-assemblies 72a, 72b of ratchet assembly 70a.

In a preferred embodiment, the retractor arm assembly 9a of the thoracic structure access system 100 comprises elongated arm member 10b, interconnector member 40, and coupling member 50e.

In a preferred embodiment, the elongated arm member 10b is similarly releasably engaged to the interconnector member 40, which similarly facilitates rotation of the elongated arm member 10b in a substantially perpendicular plane relative to its longitudinal axis "$LA_1$" when the elongated arm member 10b is operatively connected to the interconnector member 40, and the coupling member 50e is engaged to the first ratchet sub-assembly 72a of ratchet assembly 70a and also connected to the interconnector member 40.

In some embodiments, the elongated arm member 10b, interconnector member 40, and coupling member 50e similarly comprise integral members or sections of the retractor arm assembly (denoted "9c" in FIG. 5), i.e., a single member, as shown in thoracic access system 103 illustrated in FIG. 5.

As further illustrated in FIG. 2A, the elongated arm member 10b further comprises tissue retractor member 30b, which is similarly configured and adapted to receive and slidably translate over the first hexagonal shaped body region 13a of elongated arm member 10b. The tissue retractor member 30b is similarly sized, configured, and adapted to releasably engage biological tissue proximate a xiphoid incision 6 at a transxiphoid incision site 7 when the thoracic structure access system 100 is actuated, whereby, the biological tissue is spread apart, and a thoracic opening is provided at the transxiphoid incision site 7.

Figure 4B:
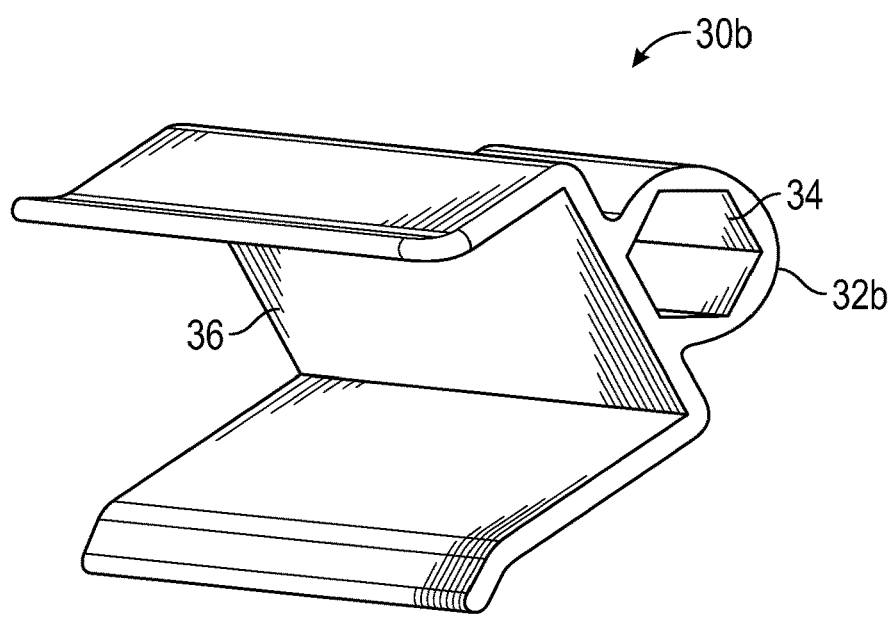
FIG. 4B is a perspective view of another embodiment of a tissue retractor member that is configured to engage biological tissue, in accordance with the invention.

As also set forth in priority U.S. application Ser. No. 17/553,992 and illustrated in FIG. 4B, the tissue retractor member 30b preferably comprises an elongated arm member engagement end 32b comprising an arm member receiving channel or opening 34 that is sized and configured to receive the hexagonal shaped body region 13a of elongated arm member 10b (and of the elongated single structure of retractor arm assembly 9b), and a tissue engaging recess 36 that is sized and configured to receive and retain biological tissue therein.

As illustrated in FIG. 2A, in a preferred embodiment, the retractor arm assembly 9a comprises at least one tissue retractor member 30b. However, according to the invention, the retractor arm assembly 9a can similarly comprise a plurality of tissue retractor members 30b.

According to the invention, the tissue retractor member(s) 30b can also be positioned at any suitable point along the length of the elongated arm member 10b.

As further illustrated in FIG. 2A, the retractor arm assembly 9a is preferably releasably engaged to ratchet assembly 70a via a coupling member 50e. The coupling member 50e similarly comprises a proximal end 58a that is sized and configured to slidably translate into a receiving channel of the interconnector member 40, e.g., receiving channel 44b, to facilitate rotation of the interconnector member 40 and, thereby, the aforementioned rotation of the elongated arm member 10b when operatively connected thereto.

As illustrated in FIG. 2A, the coupling member 50e similarly comprises a gear-tipped distal end 58b that is sized and configured to be received in and releasably engage coupling member channels 59 of first and second ratchet sub-assemblies 72a, 72b of ratchet assembly 70a.

Figure 2B:
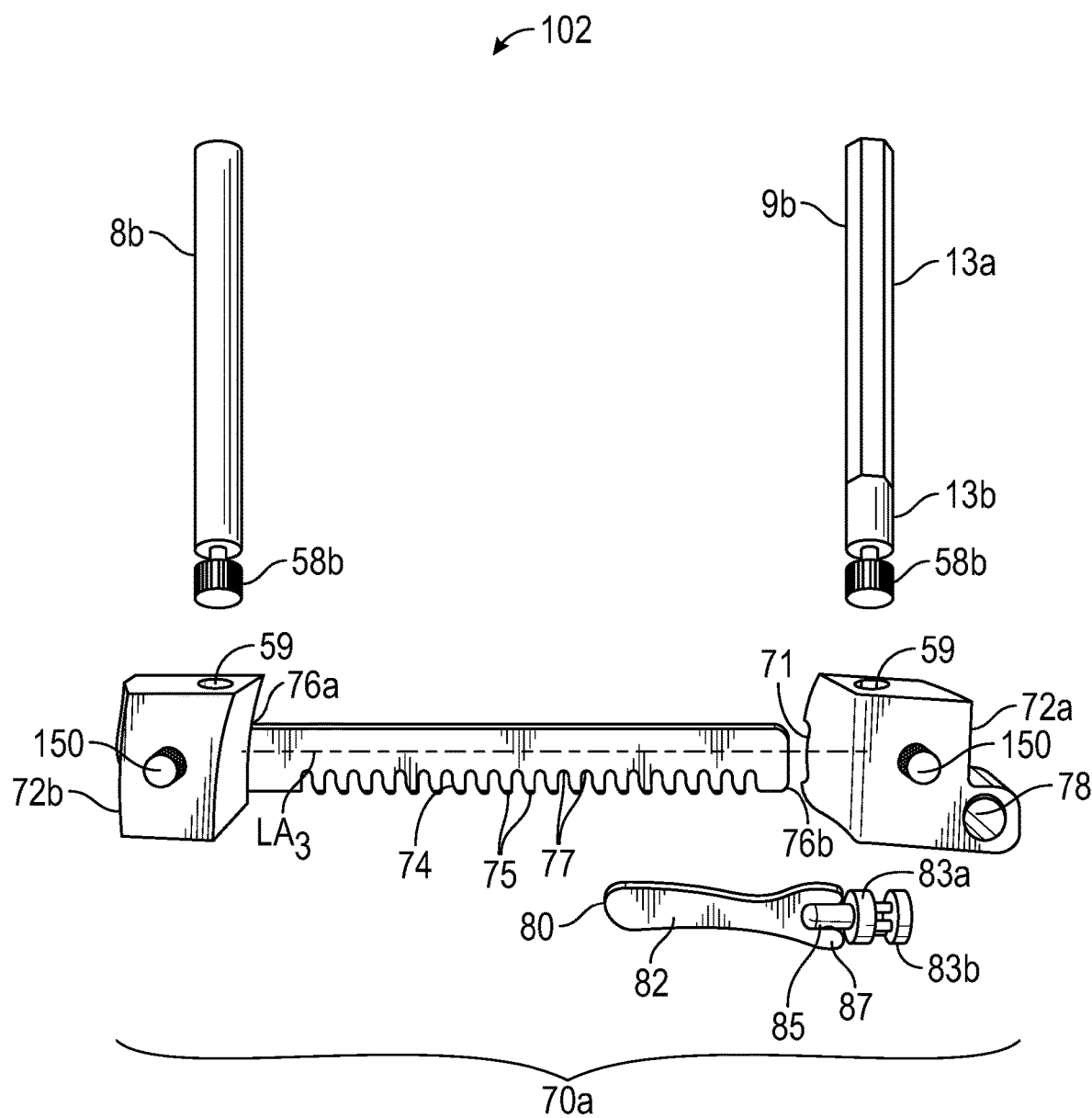
FIG. 2B is an exploded view of another embodiment of a thoracic structure access system, in accordance with the invention.

Referring now to FIG. 2B, in some embodiments of the invention, the thoracic structure access system (now denoted "102") comprises retention arm assembly 8b and retractor arm assembly 9b.

As illustrated in FIG. 2B, the retention arm assembly 8b and retractor arm assembly 9b comprise an elongated single structure that similarly comprises the gear-tipped distal end 58b, which is sized and configured to be received in and releasably engage coupling member channels 59 of first and second ratchet sub-assemblies 72a, 72b of ratchet assembly 70a. The retention arm assembly 8b and retractor arm assembly 9b are thus configured to directly engage first and second ratchet sub-assemblies 72a, 72b of ratchet assembly 70a and, hence, eliminate the need for coupling members 50d, 50e.

The thoracic structure access system 102 similarly comprises a modular system, whereby the retention arm assembly 8b and retractor arm assembly 9b can similarly be employed on different sides of the arm assembly transverse motion inducing means of the invention, discussed below.

As set forth in priority U.S. application Ser. No. 17/553, 992 and illustrated in FIG. 2A, the ratchet assembly 70a comprises toothed crossbar 74, and first and second ratchet sub-assemblies 72a, 72b, which, as shown in FIG. 2A, are configured and adapted to be mounted on toothed crossbar 74.

In a preferred embodiment, the first ratchet sub-assembly 72a and, thereby, retractor arm assembly 9a (and retractor arm assemblies 9b and 9c, if employed), is configured and adapted to laterally translate in two directions along the toothed crossbar 74.

In one embodiment of the invention, the second ratchet sub-assembly 72b and, thereby, retention arm assembly 8a (and retention arm assemblies 8b and 8c, if employed), is statically mounted to the proximal end 76a of the toothed crossbar 74.

In some embodiments of the invention, the thoracic structure access system 100 (and systems 102 and 103) comprises two of the first ratchet sub-assembly 72a; one first ratchet sub-assembly 72a being operatively connected to retractor arm assembly 9a (or retractor arm assemblies 9b and 9c, if employed) to provide lateral motion of the retractor arm assembly 9a (and retractor arm assemblies 9b and 9c) along (or parallel to) the toothed crossbar 74 and the other first ratchet sub-assembly 72a being operatively connected to retention arm assembly 8a (or retention arm assemblies 8b and 8c, if employed) to similarly provide lateral motion of the retention arm assembly 8a (and retention arm assemblies 8b and 8c) along (or parallel to) the toothed crossbar 74.

As further illustrated in FIG. 2A, the first and second ratchet sub-assemblies 72a, 72b preferably comprise pinions 150 that are configured to operatively engage with the gear-tipped distal ends 58b of coupling members 50d, 50e (and retractor and retention arm assemblies 9b, 9c and 8b, 8c, if employed) when releasably engaged to ratchet sub-assemblies 72b, 72a, respectively.

As set forth in priority U.S. application Ser. No. 17/553, 992, in a preferred embodiment, the pinions 150 are configured and adapted to rotate the coupling members 50d, 50e, whereby angular articulation of the retention arm assembly 8a and retractor arm assembly 9a (and retention and retractor arm assemblies 8b, 8c and 9b, 9c, if employed) relative to the longitudinal axes of the elongated arm members ($LA_2$ and $LA_1$) is induced, and, as discussed in detail below, the thoracic structure access system 100 (and system 102, if retention and retractor arm assemblies 8b and 9b, are employed, and system 103 if retention and retractor arm assemblies 8c and 9c, are employed) lifts the thoracic cage of a subject.

In some embodiments, the pinions 150 are manually actuated. In some embodiments, pinions 150 are electronically, e.g., computer, actuated. In some embodiments, the pinions 150 are actuated by a remotely controlled surgical system, e.g., a daVinci® Surgical System.

As set forth in priority U.S. application Ser. No. 17/553, 992, in some embodiments, the pinions 150 comprise a knurled head to accommodate actuation by a surgeon.

In some embodiments, the pinions 150 are configured and adapted to operatively connect to and, hence, cooperate with a pinion actuation tool.

Further details of the ratchet assembly 70a and the first and second ratchet sub-assemblies 72a, 72b are set forth in priority U.S. application Ser. No. 17/553,992.

Figure 6A:
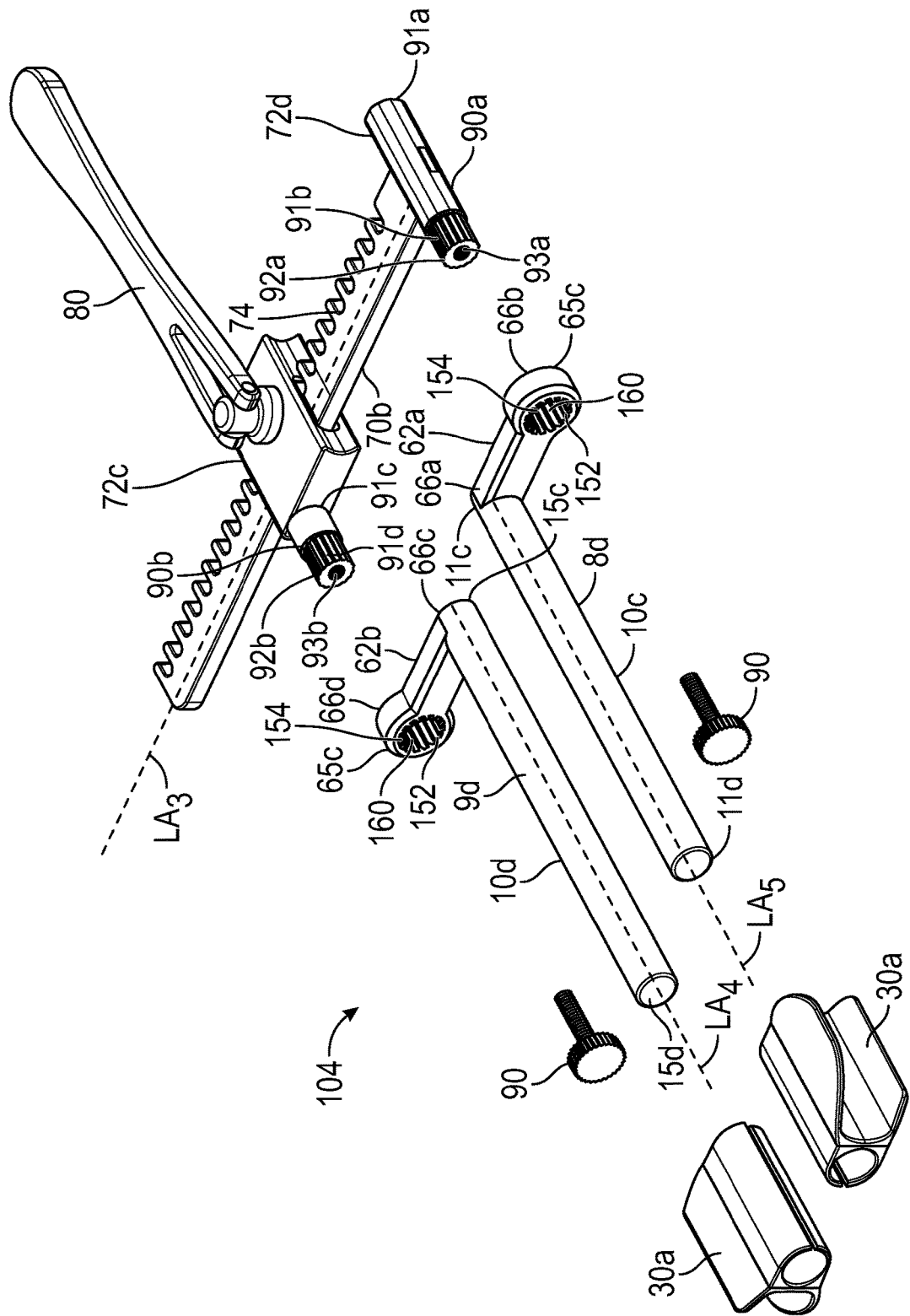
FIG. 6A is an exploded view of yet another embodiment of a thoracic structure access system, in accordance with the invention.

Referring now to FIG. 6A, there is shown another embodiment of thoracic structure access system of the invention (denoted "104").

As illustrated in FIG. 6A, the thoracic structure access system 104 similarly comprises a modular structure comprising a pair of arm assemblies and at least one arm assembly transverse motion inducing means, i.e., ratchet assembly 70b.

However, as discussed in detail below, in this embodiment, the thoracic structure access system 104 also comprises further embodiments of retention and retractor arm assemblies, and retractor sub-assemblies.

In a preferred embodiment, the retention arm assembly of the thoracic structure access system 104 (now denoted "8d") comprises an elongated arm region 10c and a base region 62a. As illustrated in FIG. 6A, the elongated arm region 10c comprises proximal and distal ends 11c, 11d. The base region 62a similarly comprises proximal and distal ends 66a, 66b; the proximal end 66a of the base region 62a being connected to the proximal end 11c of the elongated arm region 10c.

As discussed in detail below, in a preferred embodiment, the base region 62a of the retention arm assembly 8d similarly facilitates angular articulation of the elongated arm region 10c relative to its longitudinal axis $LA_5$ when the base region 62a is operatively connected to the second ratchet sub-assembly 72d.

Figure 6B:
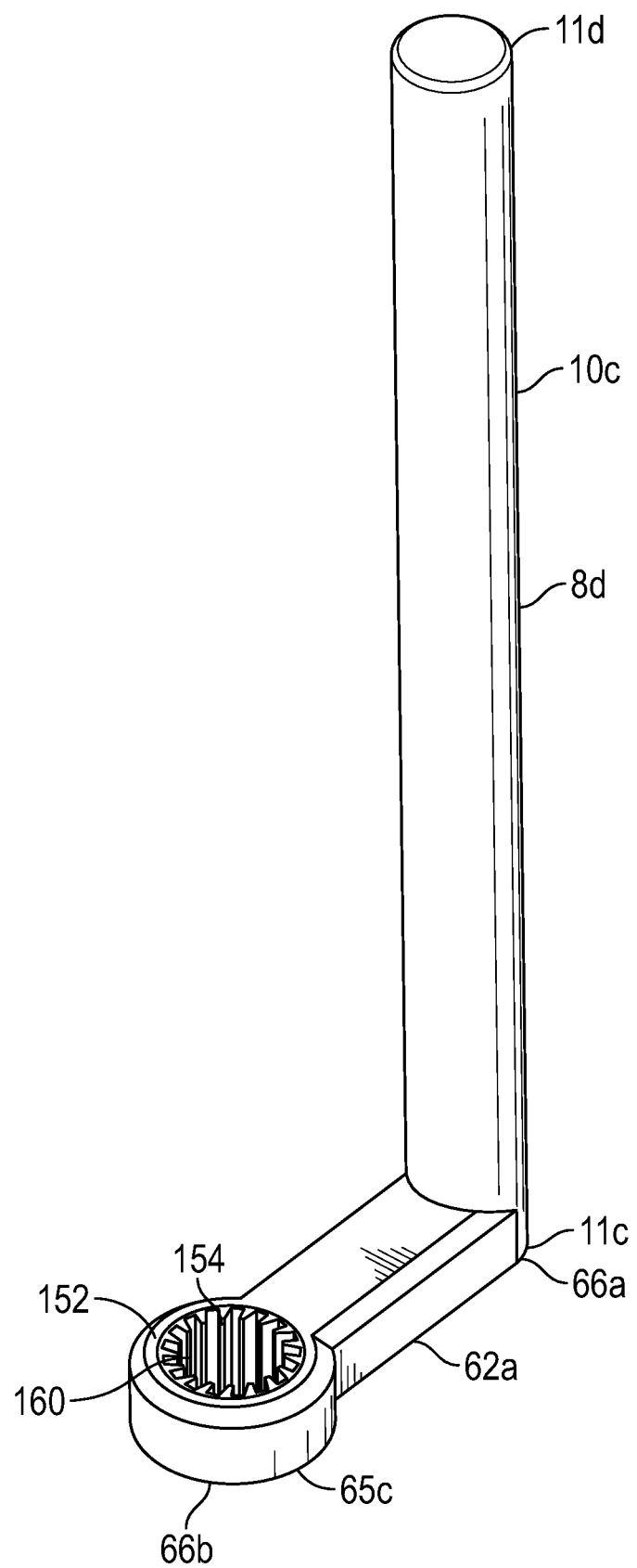
FIG. 6B is a perspective view of the retention arm assembly of the thoracic structure access system shown in FIG. 6A, in accordance with the invention.

As illustrated in FIGS. 6A and 6B, in a preferred embodiment of the invention, the base region 62a further comprises a rotatable ratchet system 160 designed and adapted to facilitate rotation of said base region 62a relative to said second ratchet sub-assembly 72d when engaged thereto.

As further illustrated in FIG. 6B, in a preferred embodiment, the distal end 66b of the base region 62a further comprises a base region lumen 65c sized and configured to receive and seat a ratchet ring gear 152 of the rotatable ratchet system 160.

As additionally illustrated in FIG. 6B, the ratchet ring gear 152 preferably comprises a plurality of internal teeth 154 adapted to receive and engage the geared end 92a of the second ratchet sub-assembly 72d (discussed below).

As also illustrated in FIG. 6A, the retention arm assembly 8d similarly comprises at least one tissue retractor member 30a, which is releasably engaged to the elongated arm region 10c.

According to the invention, the tissue retractor member(s) 30a can similarly be positioned at any suitable point along the length of the elongated arm region 10c.

As further illustrated in FIG. 6A, the retractor arm assembly of the thoracic structure access system 104 (denoted "9d") similarly comprises an elongated arm region 10d and a base region 62b. The elongated arm region 10d comprises proximal and distal ends 15c, 15d. The base region 62b similarly comprises proximal and distal ends 66c, 66d; the proximal end 66c of the base region 62b is similarly connected to the proximal end 15c of the elongated arm region 10d.

In a preferred embodiment, the base region 62b of the retractor arm assembly 9d similarly facilitates angular articulation of the elongated arm region 10d relative to its longitudinal axis $LA_4$ when the base region 62b is operatively connected to the first ratchet sub-assembly 72c.

In a preferred embodiment of the invention, the base region 62b similarly comprises the rotatable ratchet system 160 discussed above, which is adapted to facilitate rotation of said base region 62b relative to said first ratchet sub-assembly 72c when engaged thereto.

As illustrated in FIG. 6A, in a preferred embodiment, the distal end 66d of the base region 62b also similarly comprises a base region lumen 65c that is sized and configured to receive and seat the ratchet ring gear 152 of the rotatable ratchet system 160.

As further illustrated in FIG. 6A, in a preferred embodiment, the ratchet ring gear 152 is adapted to receive and engage the geared end 92b of the first ratchet sub-assembly 72c (discussed below).

As also illustrated in FIG. 6A, the retractor arm assembly 9d similarly comprises at least one tissue retractor member 30a, which is releasably engaged to the elongated arm region 10d.

According to the invention, the tissue retractor member(s) 30a can similarly be positioned at any suitable point along the length of the elongated arm region 10d.

As further illustrated in FIG. 6A, the retention arm assembly 8d is preferably releasably engaged to ratchet assembly 70b via the second ratchet sub-assembly 72d.

In a preferred embodiment, the second ratchet sub-assembly 72d comprises an elongated coupling member 90a, which is preferably statically connected to the crossbar 74 of the ratchet assembly 70b.

As further illustrated in FIG. 6A, the coupling member 90a comprises proximal and distal ends 91a, 91b; the distal end 91b comprising a geared end 92a. In a preferred embodiment, the geared end 92a of the coupling member 90a is sized and adapted to engage the ratchet ring gear 152 of base member 62a.

In a preferred embodiment, the geared end 92a of the coupling member 90a further comprises a threaded internal lumen 93a that is adapted to receive and engage retaining screw 90, which, when geared end 92a of the coupling member 90a is engaged to the ratchet ring gear 152 of base member 62a, and retaining screw 90 is engaged to the threaded internal lumen 93a, engagement of the base member 62a to the second ratchet sub-assembly 72d is maintained.

In a preferred embodiment, the retractor arm assembly 9d is preferably releasably engaged to ratchet assembly 70b via the first ratchet sub-assembly 72c. As illustrated in FIG. 6A, the first ratchet sub-assembly 72c comprises an elongated coupling member 90b, comprising proximal and distal ends 91c, 91d; the proximal end 91c being connected to the first ratchet sub-assembly 72c.

As illustrated in FIG. 6A, the distal end 91d of the coupling member 90b similarly comprises a geared end 92b that is sized and adapted to engage the ratchet ring gear 152 of base member 62b.

In a preferred embodiment, the geared end 92b of the coupling member 90b similarly comprises a threaded internal lumen 93b that is adapted to receive and engage retaining screw 90, which similarly maintains engagement of the base member 62b to the first ratchet sub-assembly 72c.

As indicated above, the thoracic structure access system 104 of the invention similarly comprises a modular system, whereby the arm assemblies 8d, 9d are interchangeable.

As illustrated in FIG. 6A, the thoracic structure access system 104 further comprises another embodiment of a ratchet assembly of the invention (denoted "70b").

The ratchet assembly 70b similarly comprises toothed crossbar 74 described above (or a similar crossbar member). However, as indicated above, the ratchet assembly 70b comprises further embodiments of ratchet sub-assemblies, i.e., first and second ratchet sub-assemblies 72c, 72d, which are similarly configured and adapted to be mounted on toothed crossbar 74.

As illustrated in FIG. 6A, the first ratchet sub-assembly 72c is slidably connected to the crossbar 74 similar to first ratchet sub-assembly 72a discussed above.

According to the invention, ratchet assembly 70b is similarly adapted to induce linear translation or movement of the first ratchet sub-assembly 72c and, thereby, retractor arm assembly 9d in first and second directions parallel to the longitudinal axis $LA_3$ of the ratchet assembly 70b.

As indicated above, the thoracic structure access systems of the invention (i.e., thoracic structure access systems 100, 102, 103, 104) are configured to retract biological tissue and provide access to internal biological structures; particularly, intrathoracic structures, e.g., the heart and internal mammary arteries, to facilitate entry through the biological tissue with surgical instruments and interaction of the surgical instruments with the intrathoracic structures during a thoracic surgical procedure; particularly, a minimally invasive CAGB and/or OPCAB procedure.

Minimally invasive methods for accessing intrathoracic structures and performing CABG and/or OPCAB procedures with the thoracic structure access systems (and associated apparatus) of the invention will now be described in detail.

In one embodiment of the invention, the first step in the minimally invasive method for providing access to intrathoracic biological tissue structures of a subject, comprises providing, assembling, and preparing a thoracic structure access system of the invention, in this instance, thoracic structure access system 104 (denoted method step "i").

According to the invention, the seminal components of the thoracic structure access system 104 can be assembled in any suitable order. Referring again to FIG. 6A, in a preferred embodiment, the thoracic structure access system 104 is assembled as follows:

(a) the first retractor sub-assembly 72c is positioned on the crossbar 74 of the retractor assembly 70b;

(b) retractor arm assembly 9d engaged to the first retractor sub-assembly 72c, as described above; and (c) retention arm assembly 8d engaged to the second retractor sub-assembly 72d, as described above.

After the retractor and retention arm assemblies 9d, 8d are engaged to coupling members 90b, 90a of first and second ratchet sub-assemblies 72c, 72d, respectively, the handle assembly 80 is actuated to laterally translate the first ratchet sub-assembly 72c along the toothed crossbar 74 towards the second ratchet sub-assembly 72d, i.e., retractor and retention arm assemblies 9d, 8d are disposed proximate each other in preparation for use during the procedure.

After thoracic structure access system 104 is prepared (denoted step "i"), a xiphoid incision 6 is made and, hence, provided at the transxiphoid incision site 7 of the subject (denoted step "ii").

After the xiphoid incision 6 is made (denoted step "ii"), the thoracic structure access system 104 is positioned proximate the xiphoid incision 6, wherein the tissue retractor members 30a of the retractor arm assembly 9d and retention arm assembly 8d are disposed proximate first and second biological tissue proximate the xiphoid incision 6 (denoted step "iii").

After the thoracic structure access system 104 is positioned proximate the xiphoid incision 6 (denoted step "iii"), the handle assembly 80 is actuated, i.e., rotated in a first direction, to laterally translate the first ratchet sub-assembly 72c and, hence, tissue retractor arm assembly 9d along toothed crossbar 74 in a first pre-determined direction, whereby (i) the tissue retractor members 30a of retractor and retention arm assemblies 9d, 8d engage the first and second tissue proximate the xiphoid incision 6, and (ii) dispose the first and second biological tissue at a spaced distance apart to provide an access space at the transxiphoid incision site 7 (denoted step "iv").

After the first and second biological tissue proximate the xiphoid incision are disposed a spaced distance apart and an open access space is provided at the transxiphoid incision site 7 (denoted step "iv"), the retractor arm assembly 9d and retention arm assembly 8d are rotated (preferably, in opposing directions), whereby the retractor arm assembly 9d and retention arm assembly 8d jointly and uniformly lift at least two opposing regions of the subject's thoracic cage (denoted step "v") and, wherein access to the intrathoracic biological tissue structures of the subject is provided.

In one embodiment of the invention, the first step in performing a minimally invasive CAGB (and/or OPCAB) procedure on a subject is similarly preparing a thoracic structure access system of the invention, in this instance, thoracic structure access system 104, as set forth above (denoted method step "i").

After thoracic structure access system 104 is prepared (denoted step "i"), a xiphoid incision 6 is similarly made and, hence, provided at the transxiphoid incision site 7 of the subject (denoted step "ii").

In a preferred embodiment, the xiphoid incision 6 is made slightly above the xiphoid process 1 and the lower portion 4 of the subject's sternum 200 and, preferably, substantially parallel with the longitudinal or craniocaudal axis of the subject 300 (denoted "$CA_1$").

According to the invention, the xiphoid incision 6 can comprise any suitable length and shape to provide an adequate working access space (and volume) for a surgeon. In a preferred embodiment, the xiphoid incision 6 comprises a length in the range of approximately 2-15 cm, more preferably, a length in the range of approximately 6-7 cm.

In a preferred embodiment, the transxiphoid incision site 7 extends from approximately 2-15 cm, more preferably, approximately 6-7 cm from below the distal end 2a of the xiphoid process 1 upwards towards subject's neck 3, as shown in FIG. 1A.

In some embodiments, transxiphoid incision site 7 is extended further downward below the distal end 2a of the xiphoid process 1.

After the xiphoid incision 6 is made at the transxiphoid incision site 7 (denoted step "ii"), a further incision is made in the pericardium of the subject's heart to accommodate insertion of surgical instruments commonly employed during a CABG (and/or OPCAB) procedure, such as an endoscope (denoted step "iii").

After the incision is made in the pericardium (denoted step "iii"), in some embodiments, an endoscope is routed into and through the incision to allow a surgeon to analyze and "inventory" the coronary arteries and internal mammary arteries to plan the CABG (and/or OPCAB) procedure based on the clinical status of the subject 300 (denoted step "iv").

By way of example, the noted analysis can include determining the distance between the internal mammary arteries (left and/or right) and the coronary arteries (left and/or right) to be bypassed to determine the necessary length of the internal mammary artery (also referred to as an internal thoracic artery) to be excised from the subject's vasculature.

It is well established that visual inspection of a subject's coronary arteries and internal mammary arteries also reveals the functional and physical characteristics of the coronary and internal mammary arteries, e.g., the texture/color of the epicardium help to indicate the severity of the stenosis. Further, the position of the coronary arteries, including whether the target arteries are "intramyocardial" (below the surface of the epicardium), will indicate the access space (and volume) required at the surgical site and in the surgical field. At this juncture, the surgeon can confirm that the transxiphoid incision site 7 is appropriate for the CABG (and/or OPCAB) procedure.

After the endoscope is routed into and through the xiphoid incision 6 (denoted step "iv"), the thoracic structure access system 104 is positioned proximate the xiphoid incision 6 (denoted step "v"), wherein the tissue retractor members 30a of the retractor arm assembly 9d and retention arm assembly 8d are disposed proximate first and second biological tissue proximate the xiphoid incision 6.

After the thoracic structure access system 104 is positioned proximate the xiphoid incision 6 (denoted step "v"), the handle assembly 80 is actuated, i.e., rotated in a first direction, to laterally translate the first ratchet sub-assembly 72c and, hence, tissue retractor arm assembly 9d along toothed crossbar 74 in a first pre-determined direction, whereby (i) the tissue retractor members 30a of retractor and retention arm assemblies 9d, 8d engage the first and second tissue proximate the xiphoid incision 6, and (ii) dispose the first and second biological tissue at a spaced distance to provide an access space at the transxiphoid incision site 7 (denoted step "vi").

After the first and second biological tissue proximate the xiphoid incision are disposed a spaced distance and an open access space is provided at the transxiphoid incision site 7 (denoted step "vi"), the retractor arm assembly 9d and retention arm assembly 8d are rotated (preferably, in opposing directions), whereby the retractor arm assembly 9d and retention arm assembly 8d jointly and uniformly lift at least two opposing regions of the subject's thoracic cage (denoted step "vii").

After the subject's thoracic cage is lifted (denoted step "vii"), at least one internal mammary artery (i.e., left or right internal mammary artery) is exposed, excised, and processed for use as a coronary artery vascular graft for the CABG (or OPCAB) procedure (denoted step "viii").

After the internal mammary artery is exposed, excised, and processed (denoted step "viii"), in some embodiments, a conventional beating heart stabilizer device, such as the beating heart stabilizer device disclosed in Applicants' U.S. Pat. No. 6,346,077, is releasably engaged to the retractor arm assembly 9d or retention arm assembly 8d (denoted step "ix").

After the beating heart stabilizer device is releasably engaged to one of the arm assemblies 8d, 9d (denoted step "ix"), the beating heart stabilizer device is actuated to render a target coronary artery substantially motionless for coronary artery bypass, i.e., providing at least one anastomotic connection between the target coronary artery and a pre-determined vascular structure (denoted step "x").

After a target coronary artery is rendered substantially motionless (denoted step "x"), the anastomotic connections are then made between a target coronary artery and a pre-determined vascular structure, e.g., an in situ vascular graft from the left internal thoracic artery to the left anterior descending coronary artery (LITA to LAD) of a subject (denoted step "xi").

In some embodiments, after the anastomotic connections are made between the target coronary artery and a pre-determined vascular structure (denoted step "xi"), another small incision is made in a subject's thorax just below the xiphoid process 1 and a drainage tube is routed from the pericardial space and through the small incision out of the subject's body (denoted step "xii").

After the drainage tube is routed from the pericardial space and through the small incision out of the subject's body (denoted step "xii"), the endoscope is again employed to check the anastomotic connections for kinking or leaks, to check the position of the drainage tube, and to check the integrity of the pleural tissue (denoted step "xiii").

In some embodiments, a conventional flow probe is employed to check the patency of the anastomotic connections.

After checking the anastomotic connections for kinking or leaks, etc. (denoted step "xiii"), the retractor arm assembly 9d and retention arm assembly 8d are rotated (preferably, in reverse directions), whereby the retractor arm assembly 9d and retention arm assembly 8d lower the subject's thoracic cage (denoted step "xiv")

After the retractor arm assembly 9d and retention arm assembly 8d are rotated (denoted step "xiv"), the handle assembly 80 is actuated again, i.e., rotated in a second direction, to laterally translate the first ratchet sub-assembly 72c and, thereby retractor arm assembly 9d along toothed crossbar 74 in a second pre-determined direction, whereby the access space at the transxiphoid incision site 7 is closed (denoted step "xv").

After the access space is closed (denoted step "xv"), the drainage tube is routed out of the small incision provided in step "xiii", and the xiphoid incision 6 is closed by the surgeon (denoted step "xvi").

As indicated above and reflected in the above procedure, when the thoracic structure access apparatus and systems of the invention are employed to access intrathoracic biological structures, the apparatus and systems substantially reduce biological tissue trauma by enabling optimal placement of biological tissue pressure points proximate a transxiphoid incision site and reducing the force/pressure applied to biological tissue structures proximate to the positions of biological tissue pressure points.

In a preferred embodiment, the thoracic structure access apparatus and systems of the invention also avoid applying force/pressure to inferior regions of a subject's costal cartilage, or shear stress to the pleural tissue of a subject, thus, sparing the costal cartilage and the pleural tissue, which results in a substantially shorter post-operative recovery time for a subject.

As will readily be appreciated by one having ordinary skill in the art, the present invention thus provides numerous advantages compared to prior art methods and systems for accessing intrathoracic biological tissue (and intrathoracic tissue structures). Among the advantages are the following:

The provision of improved thoracic structure access methods and associated systems for accessing intrathoracic biological structures in a minimally invasive manner.

The provision of improved thoracic structure access methods and associated systems for accessing intrathoracic biological structures with minimal tissue and biological structure trauma.

The provision of improved thoracic structure access methods and associated systems that provide and maintain optimal exposure and access to intrathoracic structures from a position on the lower torso of a subject.

The provision of improved thoracic structure access methods and associated systems that can be readily employed to access cardiovascular structures, including a beating heart, in a minimally invasive manner.

The provision of improved thoracic structure access methods and associated systems for performing thoracic surgical procedures; particularly, CABG and OPCAB procedures in a minimally invasive manner and, thus, with minimal tissue and biological structure trauma.

The provision of improved thoracic structure access systems that can be readily employed to perform various thoracic surgical procedures; particularly, CABG and OPCAB procedures, in a simple and economical manner.

The provision of improved thoracic structure access systems that can be readily employed to access intrathoracic structures and, thereby, perform various thoracic surgical procedures; particularly, CABG and OPCAB procedures, via a simple incision at a transxiphoid incision site and, hence, without fully transecting the sternum, i.e., performing a full sternotomy, or performing a thoracotomy.

The provision of improved thoracic structure access systems that (i) separate tissue proximate a xiphoid incision and (ii) lift multiple sections of a thoracic cage to provide optimal exposure and, thereby, access to cardiovascular structures, including a beating heart, during thoracic surgical procedures; particularly, CABG and OPCAB procedures, in a minimally invasive manner.

The provision of improved thoracic structure access systems that provide optimal exposure and accessibility to thoracic structures on both the left and right side of the body, such as the left and right internal mammary arteries (IMAs), and right and left pulmonary arteries.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A thoracic structure access system, comprising:
   a tissue retractor system configured and adapted to provide access to intrathoracic structures of a subject through a xiphoid incision proximate a xiphoid process and without fully transecting a sternum,
   said tissue retractor system comprising a tissue retractor arm assembly, a tissue retention arm assembly, and a ratchet assembly,
   said tissue retractor arm assembly comprising a first elongated arm region, a first coupling member, and a first elongated mid-arm region disposed between and connecting said first elongated arm region and said first coupling member,
   said first elongated arm region comprising a first longitudinal axis,
   said first coupling member comprising a second longitudinal axis,
   said first longitudinal axis defining a first plane and said second longitudinal axis defining a second plane, said first and second planes being substantially parallel and spaced apart a first distance,
   said first elongated mid-arm region comprising a third longitudinal axis, said third longitudinal axis being substantially perpendicular to said first longitudinal axis and said second longitudinal axis,
   said tissue retention arm assembly comprising a second elongated arm region, a second coupling member, and a second elongated mid-arm region disposed between and connecting said second elongated arm region and said second coupling member,
   said second elongated arm region comprising a fourth longitudinal axis,
   said second coupling member comprising a fifth longitudinal axis,
   said fourth longitudinal axis defining a third plane and said fifth longitudinal axis defining a fourth plane, said third and fourth planes being substantially parallel and spaced apart a second distance,
   said second elongated mid-arm region comprising a sixth longitudinal axis, said sixth longitudinal axis being substantially perpendicular to said fourth longitudinal axis and said fifth longitudinal axis,
   said ratchet assembly comprising a seventh longitudinal axis,
   said ratchet assembly comprising a crossbar, a first ratchet sub-assembly, and a second ratchet sub-assembly,
   said first ratchet sub-assembly comprising a first handle assembly and a first pinion assembly,
   said second ratchet sub-assembly comprising a second handle assembly and a second pinion assembly,
   said first ratchet sub-assembly slidably engaged to said crossbar and adapted to rotatably engage said first coupling member, whereby said first pinion assembly is in communication with said first coupling member, wherein, when said first pinion assembly is rotated, said first coupling member rotates about said second longitudinal axis of said first coupling member and induces first angular articulation of said first elongated arm region relative to said first longitudinal axis of said first elongated arm region,
   said second ratchet sub-assembly engaged to said crossbar and adapted to rotatably engage said second coupling member, whereby said second pinion assembly is in communication with said second coupling member, wherein, when said second pinion assembly is rotated, said second coupling member rotates about said fifth longitudinal axis of said second coupling member and induces second angular articulation of said second elongated arm region relative to said fourth longitudinal axis of said second elongated arm region,
   said first handle assembly operatively connected to said first ratchet sub-assembly and adapted to induce first lateral motion of said first ratchet sub-assembly and, thereby, said tissue retractor arm assembly in first and second directions in a first plane substantially parallel to said fifth longitudinal axis of said ratchet assembly, whereby said tissue retractor arm assembly transitions over a first plurality of retractor arm assembly tissue engaging positions when said first coupling member of said tissue retractor arm assembly is said rotatably connected to said first ratchet sub-assembly,
   said second handle assembly operatively connected to said second ratchet sub-assembly and adapted to induce second lateral motion of said second ratchet sub-assembly and, thereby, said tissue retention arm assembly in a third and fourth directions in a second plane substantially parallel to said fifth longitudinal axis of said ratchet assembly, whereby said tissue retention arm assembly transitions over a first plurality of retention arm assembly tissue engaging positions when said second coupling member of said tissue retention arm assembly is said rotatably connected to said second ratchet sub-assembly,
   said first plane of said first and second directions of said tissue retractor arm assembly being substantially coincident with said second plane of said third and fourth directions of said tissue retention arm assembly,
   said first elongated arm member of said tissue retractor arm assembly comprising at least a first tissue retractor member configured and adapted to releasably engage first biological tissue proximate said xiphoid incision when said tissue retractor arm assembly is in at least a first retractor arm assembly tissue engaging position of said first plurality of retractor arm assembly tissue engaging positions,
   said second elongated arm member of said tissue retention arm assembly comprising at least a second tissue retractor member configured and adapted to releasably engage second biological tissue proximate said xiphoid incision when said tissue retention arm assembly is in at least a first retention arm assembly tissue engaging position of said first plurality of retention arm assembly tissue engaging positions,
   said tissue retractor arm assembly and said tissue retention arm assembly, when said rotatably connected to said ratchet assembly and said engaged to said first and second biological tissue, being configured and adapted to dispose said first and second biological tissue a spaced distance apart, wherein an open access space proximate said subject's xiphoid process is provided, and jointly and uniformly lift opposing portions of a thoracic cage.

2. A thoracic structure access system, comprising:

a tissue retractor system configured and adapted to provide access to intrathoracic structures of a subject through a xiphoid incision proximate a xiphoid process and without fully transecting a sternum, said tissue retractor system comprising a tissue retractor arm assembly, a tissue retention arm assembly, and a linear ratchet assembly, said tissue retractor assembly further comprising a first rotatable ratchet assembly and a second rotatable ratchet assembly, said first rotatable ratchet assembly comprising a first rotatable ratchet gear, said second rotatable ratchet assembly comprising a second rotatable ratchet gear, said tissue retractor arm assembly comprising a first elongated arm region and a first base region, said first elongated arm region comprising a first arm region proximal end, a first arm region distal end, and a first longitudinal axis, said first base region comprising a first base region proximal end, a first base region distal end, and a second longitudinal axis, said first base region proximal end connected to said first arm region distal end, wherein said first longitudinal axis is substantially perpendicular to said second longitudinal axis, said first base region further comprising said first rotatable ratchet gear, said first rotatable ratchet gear comprising first internal teeth, said first rotatable ratchet gear disposed on said first base region distal end, said tissue retention arm assembly comprising a second elongated arm region and a second base region, said second elongated arm region comprising a second arm region proximal end, a second arm region distal end, and a third longitudinal axis, said second base region comprising a second base region proximal end, a second base region distal end, and a fourth longitudinal axis, said second base region proximal end connected to said second arm region distal end, wherein said third longitudinal axis is substantially perpendicular to said fourth longitudinal axis, said second base region further comprising said second rotatable ratchet gear, said second rotatable ratchet gear comprising second internal teeth, said second rotatable ratchet gear disposed on said second base region distal end, said ratchet assembly comprising a crossbar, a first ratchet sub-assembly, a second ratchet sub-assembly, and a fifth longitudinal axis, said first ratchet sub-assembly slidably connected to said crossbar, said first ratchet sub-assembly comprising a first coupling member and a first handle assembly, said first coupling member comprising a first coupling member proximal end, a first coupling member distal end, and a sixth longitudinal axis, said first coupling member proximal end connected to said first ratchet assembly, wherein said sixth longitudinal axis of said first coupling member is substantially perpendicular to said fifth longitudinal axis of said ratchet assembly, said first coupling member distal end comprising a first geared end configured and adapted to slidably engage said first rotatable ratchet gear of said first base region, wherein said first coupling member is allowed to rotate and induce first angular articulation of said first elongated arm region relative to said first longitudinal axis of said first elongated arm region, said first geared end of said first coupling member further comprising a first threaded lumen, said first ratchet sub-assembly further comprising a first retainer screw adapted to engage said first threaded lumen of said first coupling member, wherein, when said first coupling member distal end is slidably engaged to said first rotatable ratchet gear of said first base region and said first retaining screw is threadably engaged to said first threaded lumen of said first coupling member, said first retaining screw maintains said engagement of said first coupling member to said first base region of said tissue retractor arm assembly, said second ratchet sub-assembly comprising a second coupling member, said second coupling member comprising a second coupling member proximal end, a second coupling member distal end, and a seventh longitudinal axis, said second coupling member proximal end connected to said crossbar, wherein said seventh longitudinal axis of said second coupling member is substantially perpendicular to said fifth longitudinal axis of said ratchet assembly, said second coupling member distal end comprising a second geared end configured and adapted to slidably engage said second rotatable ratchet gear of said second base region, wherein said second coupling member is allowed to rotate and induce second angular articulation of said second elongated arm region relative to said second longitudinal axis of said second elongated arm region, said second geared end of said second coupling member further comprising a second threaded lumen, said second ratchet sub-assembly further comprising a second retainer screw adapted to engage said second threaded lumen of said second coupling member, wherein, when said second coupling member distal end is slidably engaged to said second rotatable ratchet gear of said second base region and said second retaining screw is threadably engaged to said second threaded lumen of said second coupling member, said second retaining screw maintains said engagement of said second coupling member to said second base region of said tissue retention arm assembly, said first handle assembly operatively connected to said first ratchet sub-assembly and adapted to induce first lateral motion of said first ratchet sub-assembly and, thereby, said tissue retractor arm assembly in first and second directions in a first plane substantially parallel to said fifth longitudinal axis of said ratchet assembly, whereby said tissue retractor arm assembly transitions over a plurality of retractor arm assembly tissue engaging positions when said first coupling member is said engaged to said first base region, said first elongated arm member of said tissue retractor arm assembly comprising at least a first tissue retractor member configured and adapted to releasably engage first biological tissue proximate said xiphoid incision when said tissue retractor arm assembly is in at least a first retractor arm assembly tissue engaging position of said plurality of retractor arm assembly tissue engaging positions, said tissue retractor arm assembly and said tissue retention arm assembly, when said connected to said ratchet assembly and said engaged to said first and second biological tissue, being configured and adapted to dispose said first and second biological tissue a spaced distance apart, wherein an open access space proximate said subject's xiphoid process is provided, and jointly and uniformly lift opposing portions of a thoracic cage.

\* \* \* \* \*